United States Patent [19]

Winkler et al.

[11] Patent Number: 4,914,221

[45] Date of Patent: Apr. 3, 1990

[54] DIMETHYLSILYL-SUBSTITUTED BENZOYL CHLORIDES AND A PROCESS FOR PREPARING THE SAME

[75] Inventors: Peter-Paul Winkler, Munich; Franz-Heinrich Kreuzer, Martinsried, both of Fed. Rep. of Germany

[73] Assignee: Consortium für Elektrochemische Industrie GmbH, Munich, Fed. Rep. of Germany

[21] Appl. No.: 229,188

[22] Filed: Aug. 8, 1988

[30] Foreign Application Priority Data

Aug. 13, 1987 [DE] Fed. Rep. of Germany ....... 3726999

[51] Int. Cl.$^4$ .............................. C07F 7/08; C07F 7/10
[52] U.S. Cl. ..................................... 556/436; 556/418
[58] Field of Search .................................. 556/436, 418

[56] References Cited

U.S. PATENT DOCUMENTS

| | | | |
|---|---|---|---|
| Re. 27,281 | 2/1972 | Wilhus et al. ................... | 556/436 X |
| 2,697,137 | 7/1953 | Frisch et al. .................... | 556/436 X |
| 2,989,559 | 6/1961 | Marsden ............................... | 556/436 |
| 3,829,455 | 8/1974 | Wilhus et al. ....................... | 556/436 |
| 4,709,084 | 11/1987 | Rich ................................... | 556/436 X |

FOREIGN PATENT DOCUMENTS 2164041  3/1986  United Kingdom ................ 556/436

*Primary Examiner*—Paul F. Shaver

[57] ABSTRACT

The invention relates to dimethylsilyl-substituted benzoyl chlorides and a process for preparing the same, which comprises reacting a dihaloaromatic compound with dimethylchlorosilane and magnesium by the Grignard method to form halophenyldimethylsilanes, then reacting the halophenyldimethylsilanes with magnesium in the presence of carbon dioxide to form the corresponding dimethylsilyl-substituted benzoic acids, and thereafter reacting the dimethylsilyl-substituted benzoic acids with a halogenating agent, such as thionyl chloride, to form dimethylsilyl-substituted benzoyl chlorides.

4 Claims, No Drawings

DIMETHYLSILYL-SUBSTITUTED BENZOYL CHLORIDES AND A PROCESS FOR PREPARING THE SAME

The invention relates to dimethylsilyl-substituted benzoyl chlorides, and more particularly to a process for preparing the same from dihaloaromatic compounds.

BACKGROUND OF THE INVENTION

Difunctional silanes which are both silicon-functional and contain organofunctional groups are known and employed in many areas of industry. Thus, for example, they have been used as adhesion promoters in glass fiber-reinforced polyester and epoxy laminates (cf. E. P. Plueddemann et al. in "Mod. Plast." 1962 (8), pp. 135 ff.). Also, they have been used, for example, in the production of specialty tires, in the production of liquid-crystal displays, in the production of textile fibers and metal (oxide) electrodes, according to the review by U. Deschler, P. Kleinschmit and P. Panster in "Angew. Chemie" Vol. 98, pp. 237–253 (1986).

Hydrogensilanes containing a carbonyl chloride function as an organofunctional group should be of interest in this regard. The H-silane function can, for example, be added to alkenes and alkynes, then converted into halosilanes, alkoxysilanes, acyloxysilanes or aminosilanes, or employed in the formation of siloxane bonds; whereas, the carbonyl chloride function is capable of reacting with hydroxyl, mercapto or amino-containing compounds.

Therefore, it is an object of the present invention to prepare dimethylsilyl-substituted benzoyl chlorides. Another object of the present invention is to provide a process for preparing dimethylsilyl-substituted benzoyl chlorides. Still another object of the present invention is to provide a process for preparing dimethylsilyl-substituted benzoyl chlorides in high yields. A further object of the present invention is to provide a process for preparing dimethylsilyl-substituted benzoyl chlorides as intermediates which are capable of reacting with compounds containing reactive groups.

SUMMARY OF THE INVENTION

The foregoing objects and others which will become apparent from the following description are accomplished in accordance with this invention, generally speaking, by providing dimethylsilyl-substituted benzoyl chlorides of the general formula

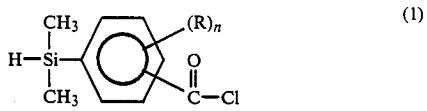

(1)

in which R is selected from the group consisting of fluorine atoms, alkyl radicals having from 1 to 8 carbon atoms, which may be branched or straight-chain and may be substituted by alkoxy, alkenyloxy, aryloxy or dialkylamino groups, alkenyl radicals having from 2 to 8 carbon atoms, which may be straight-chain or branched, alkoxy, alkenyloxy or aryloxy radicals having up to 8 carbon atoms, or dialkylamino groups having from 1 to 3 carbon atoms per alkyl radical, and n is 0 or 1, and a process for preparing the same.

DESCRIPTION OF THE INVENTION

In the dimethylsilyl-substituted benzoyl chlorides represented by the above formula, the radicals represented by R are fluorine, methyl, ethyl, n-propyl, i-propyl, n-butyl, methoxymethyl, ethoxymethyl, allyloxymethyl, phenoxymethyl, dimethylaminomethyl, diethylaminomethyl, 1-propenyl, 2-propenyl, methoxy, ethoxy, n-propoxy, n-butoxy, allyloxy, phenoxy, dimethylamino, diethylamino and dipropylamino radicals.

Preferred radicals represented by R are fluorine, methyl, ethyl, methoxymethyl, allyloxymethyl, phenoxymethyl, dimethylaminomethyl, allyl, methoxy, allyloxy, phenoxy, dimethylamino and diethylamino radicals.

The COCl and R radicals may in each case be arranged in the 2-, 3-, or 4-position on the benzene ring with respect to the silyl radical.

The dimethylsilyl-substituted benzoyl chlorides (1), which heretofore had not been described in the literature, are valuable and versatile intermediates.

The dimethylsilyl-substituted benzoyl chlorides (1) of this invention can be prepared in three steps, from dihaloaromatic compounds in accordance with the following procedure.

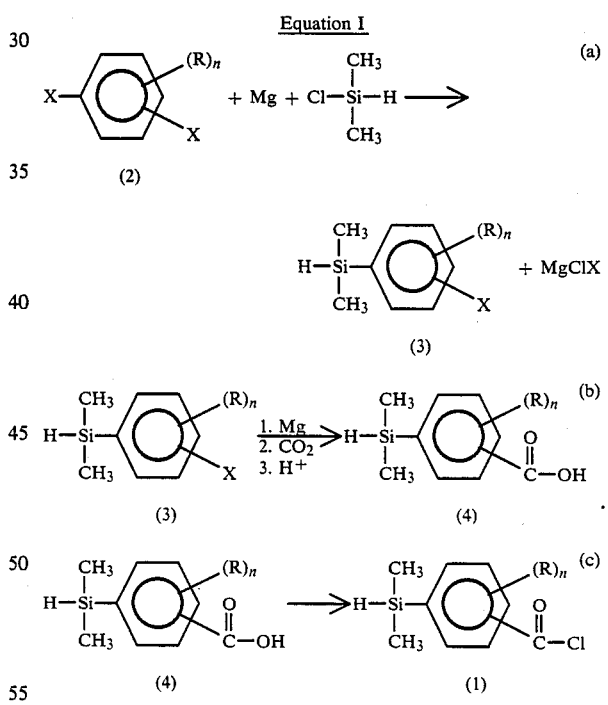

In the above formulas, R and n are the same as above and X represents the Cl or Br atom.

Heretofore, a two-step method was known for preparing halophenyldimethylsilanes, such as, for example, (4-chlorophenyl)dimethylsilane.

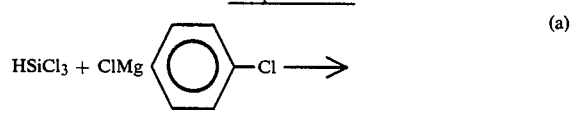

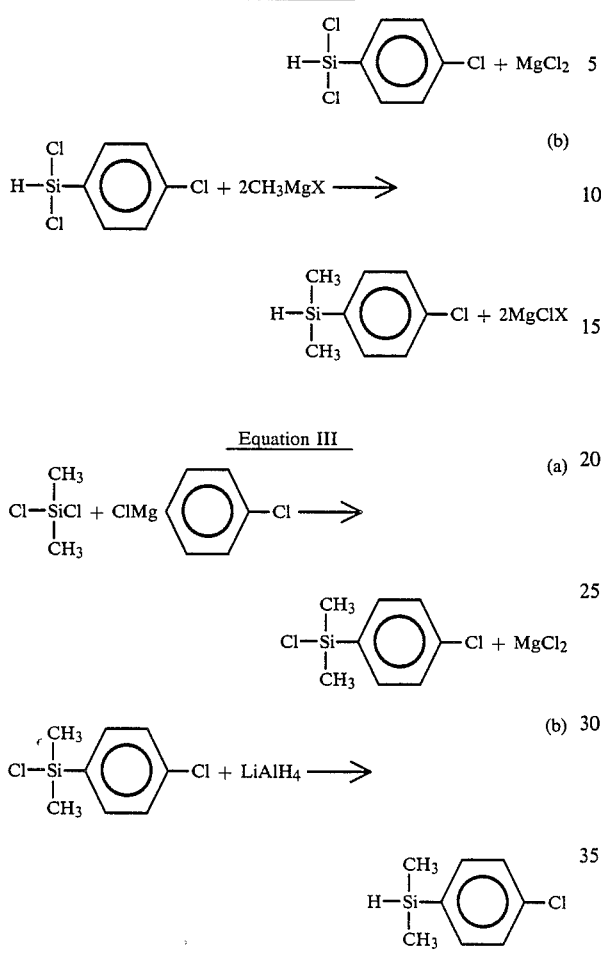

In the method represented by Equation II, 3 moles of magnesium are required, which makes the process very expensive. Moreover, the yield was not mentioned in the article by J. E. Baines, C. Eaborn, in "J. Chem. Soc.", p. 1436 (1956).

In the second synthetic method, LiAlH$_4$ was required as the reducing agent, which is, likewise, very expensive, and in addition, requires special safety precautions for handling the reducing agent. The yield in this synthesis was 40 percent [cf. G. Gerber, A. Balciunas, in "Makromol. Chem.", Vol. 71, p. 62 (1964)].

In contrast to the procedure described above for the preparation of, for example (4-chlorophenyl)dimethylsilane in accordance with Equation I(a) from dimethylchlorosilane and 1,4-dichlorobenzene, a yield of 70 percent was obtained.

The silane employed as starting material is a byproduct of the Rochow synthesis.

According to this invention, the substituted halophenyldimethylsilanes of formula (3) are prepared by preparing the mono-Grignard compound from dihaloaromatic compounds (2), and reacting the former with dimethylchlorosilane in accordance with Equation I(a).

In carrying out this process step, the substituted halophenylmagnesium halides are preferably prepared in a straight chain or cyclic ether as solvent. Preferred solvents are tetrahydrofuran and 1,2-dimethoxyethane. The reaction temperature should preferably be between 50° and 70° C., when X is chlorine and between 20° and 60° C. when X is bromine.

In the preparation of the halophenylmagnesium halides, higher temperatures, such as those obtained under the conditions specified in the literature [cf. J. R. Leebrick, H. E. Ramsden, in "J. Org. Chem.", Vol 23, p. 935 (1958)], should be avoided since relatively large amounts of di-Grignard compound are otherwise formed.

The reaction may be accelerated by the addition of from 0.1 to 5 mol percent of anthracene.

In the preparation of the silane compounds (3), the Grignard solution is preferably added to a solution of dimethylchlorosilane in an inert solvent. Examples of inert solvents are benzene, toluene and methyl tert-butyl ether, in addition to the solvents used for the Grignard reaction.

The silane compounds (3) can also be prepared by adding dimethylchlorosilane and the dihaloaromatic compound (2) in a solution of one of the abovementioned solvents, to the magnesium so that the reaction which forms the product (3), and the Grignard compound in situ, takes place. The magnesium chloride can be removed from the reaction mixture by filtration or by adding water and separating off the organic phase. The solution of crude product is evaporated and distilled.

The dimethylsilyl-substituted benzoic acids (4) are prepared according to the invention in accordance with Equation I(b) by reacting the substituted halophenyldimethylsilanes (3) with magnesium to form the appropriate Grignard compounds, which are then reacted with carbon dioxide to form the carboxylic acid salts. The benzoic acids are liberated from the magnesium salts by acidification.

The Grignard reaction is carried out in a suitable solvent. Examples of such solvents are straight chain and cyclic ethers, such as diethyl ether, tetrahydrofuran, dimethoxyethane and diethylene glycol dimethyl ether. The preferred solvent is tetrahydrofuran.

The reaction temperature may be between 30° and 100° C. In order to achieve a suitable reaction rate while keeping the formation of byproducts to a minimum, the reaction should preferably be carried out between 50° and 80° C. when X is chlorine and when X is bromine, the reaction temperature may be between 20° and 80° C. Magnesium can be employed in the form of powder or turnings. The reaction may be accelerated by the addition of from 0.1 to 5 mol percent of anthracene.

The reaction of the substituted dimethylsilylphenylmagnesium chlorides with carbon dioxide can be carried out by introducing dry ice or by blowing gaseous CO$_2$ or carbon dioxide snow into the reaction solution.

The reaction preferably takes place by the slow addition of the Grignard solution to a saturated solution of carbon dioxide in tetrahydrofuran. The reaction temperature can be between −40° and +40° C.

The dimethylsilyl-substituted benzoic acids (4) are liberated from their magnesium salts by acidifying the reaction mixture using dilute hydrochloric acid or dilute sulfuric acid at pH 3. Purification of the products takes place by separating off and evaporating the organic phase. The product crystallizes out. The compound can be purified by distilling the crude product. Also, the product can be crystallized quantitatively by adding a nonpolar solvent such as petroleum ether, and additional purification can be carried out by recrystallizing the product from the solvent.

According to this invention, the synthesis of the dimethylsilyl-substituted benzoyl chlorides (1) takes place in accordance with Equation I(c) by chlorinating the dimethylsilyl-substituted benzoic acids (4) with halogenating agents. Examples of halogenating agents are phosphorus pentachloride, phosphorus trichloride, phosgene, oxalyl chloride and thionyl chloride. The preferred halogenating agent is thionyl chloride. The reaction may be carried out in a diluent, for example, inert solvents, such as hydrocarbons, halogenated hydrocarbons and ethers. Nonpolar solvents, such as aliphatic, branched or linear hydrocarbons, or aromatic hydrocarbons are preferred. Examples of particularly preferred solvents are benzene, toluene, xylene, hexane and heptane. The reaction temperature may be in the range of from 0° C. and the boiling point of the reaction mixture, but a reaction temperature of from 40° to 80° C. is preferred. If desired, a reaction accelerator may be added. Examples of reaction accelerators are pyridine and dimethylformamide. If thionyl chloride is used as the halogenating agent, the crude product can be used for further syntheses after completion of the gas evolution, or the pure substance can be removed after evaporation of the solvent and distillation.

The synthesis of the dimethylsilyl-substituted benzoyl chlorides of formula (1) in good yields by reacting the dimethylsilyl-substituted benzoic acids (4) with thionyl chloride under maintenance of the H-silane function must be regarded as surprising since several side reactions were expected from this synthesis. Thus, for example, it is known that the hydrogen halide produced during the reaction is capable of cleaving the Si-H bond or the Si-C bond [cf. W. Noll, chemie und Technologie der Silicone, (Chemistry and Technology of the Silicones), p. 80, Verlag Chemie 1968, 2nd edition]. It is further known that acid chlorides can be reduced to aldehydes by H-silanes [cf. J. W. Jenkins, H. W. Post in "J. Organ. Chem.", vol, 15, p. 556 (1950)]. In addition, a redox reaction, for example, with thionyl chloride to form the chlorosilane, can take place due to the reducing properties of the H-silanes [cf. S. Pawlenko in: "Methoden der organischen Chemie" (Methods of organic chemistry) (Hoben-Weyl), Vol. 13/5, pp. 350 ff, Georg Thieme Verlag Stuttgart 1980, 4th edition]. Also, it is known that carbonyl compounds can be reduced by H-silanes in an acidic medium. (cf. in loco citato).

The only known example of the precursors (4) is (4-dimethylsilyl)benzoic acid. The synthesis takes place in a 23 percent yield from (4-bromophenyl)dimethylsilane [cf. F. Mares, P. Neudorfel, Z. Plzak, V. Chvalovski, in "Collect. Czech. Chem. Commun.", Vol. 35, p. 2324 (1970)]. According to this invention, (4-dimethylsilyl)benzoic acid is prepared in a 68 percent yield from less expensive (4-chlorophenyl)dimethylsilane in accordance with Equation I(b).

EXAMPLE (a) Preparation of (4-chlorophenyl)dimethylsilane in accordance with Equation I(a):

About 9 kg of 1,4-dichlorobenzene (60 mol) were dissolved in 10.2 liters of tetrahydrofuran. About 1,440 g of magnesium turnings activated with iodine were introduced into a 50 liter stirred kettle. About 1.4 liters of tetrahydrofuran and 600 ml of 1,4-dichlorobenzene solution were then added, and the mixture was warmed to 50° C. The reaction was initiated by adding a few ml of ethyl bromide. The dichlorobenzene solution was added over a period of about 4 hours, the reaction temperature being kept between 60° and 63° C. When all the dichlorobenzene had been added, the reaction mixture was allowed to stand for 2.5 hours at 60° C. to complete the reaction. The reaction mixture was then cooled, diluted with 6 liters of tetrahydrofuran and transferred into a dropping funnel. The conversion was determined by weighing the unreacted magnesium. It was 88 percent by weight. Accordingly, 52.9 mol of dimethylchlorosilane in 12 liters of methyl tert-butyl ether were introduced into the 50 liter stirred kettle. The Grignard solution was added through the dropping funnel at a rate such that it was possible to keep the temperature at 30° C. with cooling. The reaction mixture was then stirred for an additional 30 minutes at room temperature. Sufficient water was added to the crystal slurry so that two homogeneous phases formed. The organic phase was separated off, and the aqueous phase was extracted once with methyl tert-butyl ether. The crude product was distilled in a water-pump vacuum. About 6,305 g of (4-chlorophenyl)dimethylsilane were obtained, which amounted to a yield of about 70 percent by weight, based on the amount of dichlorobenzene reacted.

Boiling point: 77° to 80° C./15 hPa.

(b) Preparation of (4-dimethylsilyl)benzoic acid in accordance with Equation I(b):

About 72 g of magnesium turnings were introduced into a round-bottomed flask and activated using iodine. A solution comprising 508.5 g (4-chlorophenyl)dimethylsilane in 650 ml of tetrahydrofuran was prepared in the dropping funnel. About 100 ml of the silane solution were added dropwise, while the temperature was adjusted to 60° C., and the reaction was initiated using ethyl bromide. The remaining silane solution was added dropwise over a period of 3.5 hours. During this addition, the temperature was maintained at 60° C. When the addition was complete, the reaction mixture was allowed to stand for two hours at 60° C. to complete the reaction. A gray-white suspension was obtained. The conversion was 78 percent. Unreacted magnesium was removed, and the suspension was transferred into a dropping funnel. One liter of tetrahydrofuran was then saturated with gaseous carbon dioxide and introduced slowly into the Grignard compound at 15° to 25° C. under a constant stream of $CO_2$. After one hour, all the Grignard compound had been added, and the mixture was stirred for an additional 20 minutes while continuing to introduce $CO_2$. The reaction mixture was then slowly transferred into about 250 ml of water. The pH of the 2-phase system was at the same time kept at pH 5 by adding dilute HCl. The pH was finally adjusted to 3. The organic phase was separated off, and the aqueous phase was extracted with methyl tert-butyl ether. The organic phases were combined and evaporated. The viscous solution crystallized overnight. For improved crystallization, a little petroleum ether was added, and the crystals filtered off. The crystals were washed with petroleum ether and dried. The mother liquor was subsequently crystallized. About 275 g of (4-dimethylsilyl)benzoic acid were obtained which amounted to a yield of about 67.8 percent by weight, based on the amount of (4-chlorophenyl)dimethylsilane reacted.

Boiling point: 109° to 112° C./0.13 hPa.

(c) Preparation of (4-dimethylsilyl)benzoyl chloride in accordance with Equation I(c):

About 173 g of (4-dimethylsilyl)benzoic acid (0.96 mol) were dissolved in 150 ml of toluene, and then 117 g of thionyl chloride (0.96 mol) were added. The mixture was warmed at 50° C. for eight hours, during which SO₂ and HCl were evolved. The solvent was stripped off and the residue was distilled. About 171.4 g of (4-dimethylsilyl)benzoyl chloride were obtained, which amounted to a yield of about 90.3 percent by weight.

Boiling point: 64° C./0.03 hPa.

$^1$H-NMR (CDCl$_3$): 8.00 ppm (d, 8 Hz, 2H), 7.50 ppm (d, 8 Hz, 2H), 4.44 ppm (septet, 3.5 Hz, 1H), 0.37 ppm (d, 3.5 Hz, 6H)

What is claimed is:

1. A dimethylsilyl-substituted benzoyl chloride of the formula

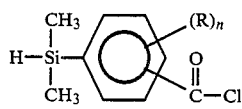 (1)

in which R is selected from the group consisting of alkyl radicals having from 1 to 8 carbon atoms, alkyl radicals substituted with a group selected from the group consisting of fluorine atoms alkoxy, alkenyloxy, aryloxy and dialkylamino groups, alkenyl radicals having from 2 to 8 carbon atoms, alkoxy, alkenyloxy or aryloxy radicals having up to 8 carbon atoms and dialkylamino groups having from 1 to 3 carbon atoms per alkyl radical, and n is 0 or 1, in which the COCl and R radicals are each arranged in the 2-, 3- or 4-position on the benzene ring to the silyl radical.

2. (4-Dimethylsilyl)benzoyl chloride.

3. A process for preparing the dimethylsilyl-substituted benzoyl chloride of claim 1, which comprises (a) reacting a dihaloaromatic compound of the formula

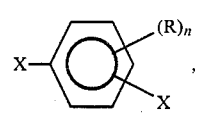 (2)

in which R is selected from the group consisting of fluorine atoms, alkyl radicals having from 1 to 8 carbon atoms, alkyl radicals substituted with a group selected from the group consisting of alkoxy, alkenyloxy, aryloxy and dialkylamino groups, alkenyl radicals having from 2 to 8 carbon atoms, alkoxy, alkenyloxy or aryloxy radicals having up to 8 carbon atoms and dialkylamino groups having from 1 to 3 carbon atoms per alkyl radical and X is selected from the group consisting of chlorine and bromine atoms and n is 0 or 1 with dimethylchlorosilane and magnesium by the Grignard method to form a halophenyldimethylsilane of the formula

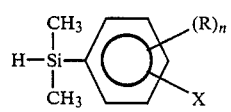 (3)

(b) reacting the halophenyldimethylsilane (3) with magnesium by the Grignard method in the presence of carbon dioxide to form a dimethylsilyl-substituted benzoic acid of the formula

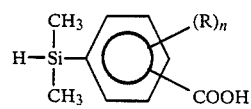 (4)

and thereafter (c) reacting the dimethylsilyl-substituted benzoic acids (4) with a chlorinating agent to form the dimethylsilyl-substituted benzoyl chloride (1).

4. The process of claim 3, wherein the chlorinating agent is thionyl chloride.

* * * * *